(12) United States Patent
Frank et al.

(10) Patent No.: US 8,332,023 B2
(45) Date of Patent: Dec. 11, 2012

(54) METHOD FOR IDENTIFYING AN R-WAVE IN AN ECG SIGNAL, ECG MEASURING DEVICE AND MAGNETIC RESONANCE SCANNER

(75) Inventors: Michael Frank, Erlangen (DE); Jürgen Rößler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 396 days.

(21) Appl. No.: 12/694,403

(22) Filed: Jan. 27, 2010

(65) Prior Publication Data
US 2010/0191134 A1    Jul. 29, 2010

(30) Foreign Application Priority Data

Jan. 28, 2009 (DE) .......................... 10 2009 006 391
Mar. 27, 2009 (DE) .......................... 10 2009 015 385

(51) Int. Cl.
*A61B 5/0456* (2006.01)

(52) U.S. Cl. ....................................................... 600/521
(58) Field of Classification Search ................... 600/521
See application file for complete search history.

(56) References Cited

U.S. PATENT DOCUMENTS 4,023,564 A * 5/1977 Valiquette et al. ............ 600/517
4,617,938 A * 10/1986 Shimoni et al. ............... 600/521
5,388,578 A * 2/1995 Yomtov et al. ................ 600/375

FOREIGN PATENT DOCUMENTS

DE     102005027438 A1    12/2006
DE     102006058332 A1    6/2008

* cited by examiner

*Primary Examiner* — Niketa A Patel
*Assistant Examiner* — Alyssa M Alter (57) ABSTRACT

An ECG measuring device and a magnetic resonance scanner to permit reliable detection of R-waves in ECG signals. The R-waves are identified by: measuring at least one reference ECG signal by an ECG measuring device, identifying an R-wave in the reference ECG signal, determining from the reference ECG signal at least one reference quantity which the reference ECG signal assumes in a time interval that starts before the R-wave of the ECG signal and lasts at a maximum up to the occurrence of the R-wave, generating at least one comparison rule on the basis of the at least one reference quantity, measuring ECG signals in which R-waves are to be identified, comparing the measured ECG signals with at least one reference quantity on the basis of the at least one comparison rule and outputting a trigger signal on the basis of at least one positive result of the comparison.

19 Claims, 4 Drawing Sheets

METHOD FOR IDENTIFYING AN R-WAVE IN AN ECG SIGNAL, ECG MEASURING DEVICE AND MAGNETIC RESONANCE SCANNER

CROSS REFERENCE TO RELATED APPLICATIONS

This application claims priority of German application No. 10 2009 006 391.9 filed Jan. 28, 2009, and German application No. 10 2009 015 385.3 filed Mar. 27, 2009, both of the applications are incorporated by reference herein in their entirety.

FIELD OF THE INVENTION

The invention relates to a method for identifying an R-wave in an ECG signal, an ECG measuring device and a magnetic resonance scanner

BACKGROUND OF THE INVENTION

ECG measuring devices are used primarily for measuring and monitoring a patient's cardiac function, for which purpose the summation voltage of the electrical activity of the myocardial fibers is typically measured across at least two electrodes as what is termed an "ECG signal". An ideal waveform of an ECG signal of said kind is shown by way of example in FIG. 1 as voltage U over time. According to Einthoven, characteristic waveforms of the ECG signal are designated by the letters P, Q, R, S and T and generally reflect the different phases of a heartbeat.

There are other applications in addition to the pure monitoring of a patient's cardiac function. For example, ECG signals are also used in medical imaging applications for the purpose of generating trigger signals. During imaging, information about the cardiac cycle is acquired via the ECG signal in order thereby to synchronize the imaging with the cardiac activity. In particular with imaging methods that require a relatively long recording time, high-quality images of the heart or images of regions that are moved by the heartbeat can be recorded in this way.

ECG measuring devices are also used for in-situ recording of ECG signals during an examination of a patient by means of a magnetic resonance scanner. In this case, however, operation in the magnetic resonance scanner imposes special requirements on the ECG measuring device due to the strong gradient fields and radio-frequency fields used there for the imaging in order to prevent mutual interference between magnetic resonance scanner and ECG measuring device. ECG measuring devices that are magnetic-resonance-compatible in the aforementioned sense are available on the market.

Identifying R-waves in ECG signals is essential for reliable triggering. Said identification is, however, made more difficult e.g. as a result of T-wave overshoots occurring in the magnetic field.

Magnetic fields that change over time, as used in the magnetic resonance scanner as magnetic gradient fields for position encoding, also continue to represent a further major problem for reliable ECG signal measurement. According to the law of induction, temporally fluctuating magnetic fields of said type generate interference voltages which are coupled into the ECG signal recorded by the ECG electrodes as noise. Magnetically generated interference signals of said kind become superimposed on the ECG signal generated by the heart and distort said signal.

These sources of interference are extremely undesirable. Reliable detection of the R-wave of the ECG signal is necessary in order to synchronize a recording of a magnetic resonance image with the heartbeat. The noise signals can be erroneously interpreted as an R-wave e.g. due to their often similar shape and consequently can incorrectly initiate a triggering of a recording of a magnetic resonance image. On the other hand it can also happen that a "real" R-wave is not detected as such due to the superimposed noise signals. This frequently leads to a significant deterioration in image quality.

Prior art attempts to solve this problem consisted in subjecting signals interpreted as a possible R-wave to a simple threshold value check in addition prior to a triggering. Said threshold value check generally provides a maximum value that is not to be exceeded and a minimum value that is not to be undershot. If the maximum value is exceeded, it is assumed that a parasitic induction was present due to the gradient fields. If the minimum value is undershot, it is assumed that a T-wave has erroneously been interpreted as an R-wave. In both cases no trigger signal is output.

SUMMARY OF THE INVENTION

It is therefore the object of the invention to disclose a method, an ECG measuring device and a magnetic resonance scanner which permit reliable detection of R-waves of ECG signals measured in the magnetic resonance scanner.

The object is achieved according to the invention by a method and an ECG measuring device and a magnetic resonance scanner as claimed in the claims In this case an inventive method for identifying R-waves in an ECG signal for the purpose of triggering further measurements or examinations comprises the following steps:
  measuring at least one reference ECG signal by means of an ECG measuring device,
  identifying an R-wave in the reference ECG signal,
  determining from the reference ECG signal at least one reference quantity which the reference ECG signal assumes in a time interval that starts before the R-wave of the ECG signal and lasts at a maximum up to the occurrence of the R-wave,
  generating at least one comparison rule on the basis of the at least one reference quantity,
  measuring ECG signals in which R-waves are to be identified,
  comparing the measured ECG signals with the at least one reference quantity on the basis of the at least one comparison rule,
  outputting a trigger signal on the basis of at least one positive result of the comparison.

By means of the analysis of ECG signals that is possible by means of the method in a time interval before the event of interest, the occurrence of an R-wave, on the one hand time is gained for said analysis until a trigger signal can be output when an R-wave is present, since not only is a potential event of interest analyzed as instantaneously as possible, but an ECG signal is checked over a relatively long period of time. At the same time this also increases the reliability of the analysis and consequently the reliability of the identification of an R-wave.

An ECG measuring device according to the invention comprises a processing unit, a computing unit and a memory unit which interact in such a way that a method according to the invention can be performed.

A magnetic resonance scanner according to the invention comprises an ECG measuring device, a processing unit, a computing unit and a memory unit which interact in such a way that a method according to the invention can be performed, wherein the output trigger signal is used for the purpose of triggering measurements by means of the magnetic resonance scanner.

The method-related advantages apply analogously to an inventive ECG measuring device and an inventive magnetic resonance scanner.

BRIEF DESCRIPTION OF THE DRAWINGS

Further advantages and details of the present invention will emerge from the exemplary embodiments described hereinbelow as well as with reference to the drawings. The examples presented constitute no limitation of the invention.

DETAILED DESCRIPTION OF THE INVENTION

Figure 2:
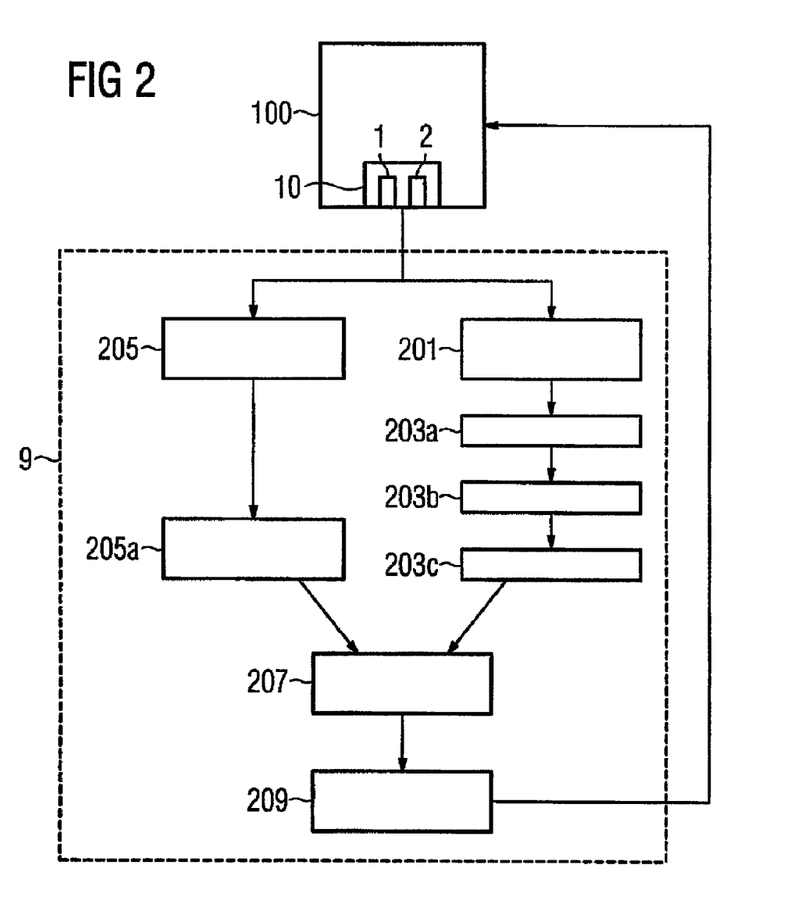
FIG. 2 is a schematic representation of an execution sequence of the method according to the invention in conjunction with an ECG measuring device and a magnetic resonance scanner, FIG. 3 schematically shows an ECG measuring device.

The method according to the invention in conjunction with an ECG measuring device and a magnetic resonance scanner is explained below with reference to FIGS. 2 and 3.

During an examination, a patient having an attached ECG measuring device 10 is positioned in the magnetic resonance scanner 100. The magnetic resonance scanner 100 and the ECG measuring device are represented in this case only schematically as a block, since the basic layout consisting of magnet unit, radio-frequency coils, gradient coil unit, examination table, and control units of a magnetic resonance scanner is known, as also is the basic layout of an ECG measuring device comprising ECG electrodes and amplifier/filter units for measuring a voltage between two ECG electrodes.

According to the invention the magnetic resonance scanner 100 comprises in particular an ECG measuring device 10, a processing unit 9, a computing unit 8 and a memory unit 8a. The separate or combined representation of said units is to be understood not necessarily physically, but rather as a separation or combination based on meaningful entities.

The ECG measuring device 10, the processing unit 9, the computing unit 8 and the memory unit 8a are connected to the magnetic resonance scanner 100 and to one another for the purpose of transmitting data.

In this case the ECG measuring device 10 is advantageously represented here as comprising two ECG channels 1 and 2. The method according to the invention can also be performed using ECG measuring devices having only one or more than two ECG channels, though, as will be explained in greater detail below, two ECG channels are already sufficiently suitable for a particularly reliable and low-overhead identification of R-waves in ECG signals.

In such an arrangement one ECG channel 1,2 outputs an ECG signal which the ECG measuring device determines from a voltage between two ECG electrodes (not shown) attached to the patient.

In a first step 201 of the method, at least one reference ECG signal is measured at a channel 1,2 of the ECG measuring device 10. In this case the at least one reference ECG signal is recorded in an environment that is undisturbed by external influences, e.g. in the magnet of the magnetic resonance scanner 100, without gradient fields being switched on in the magnetic resonance scanner 100. In a further step 203a, the R-wave is identified in the reference ECG signal, e.g. in one of the ways known in the prior art.

Next (step 203b), there is determined from the at least one reference ECG signal at least one reference quantity which the reference ECG signal assumes in a time interval which starts before the R-wave of the ECG signal and lasts at a maximum up to the time of the occurrence of the R-wave. Thus, the reference quantity can also be a variation of a value determined from the ECG signal over a period of time in the time interval.

In this case the size of the time interval can largely be freely specified.

Figure 1:
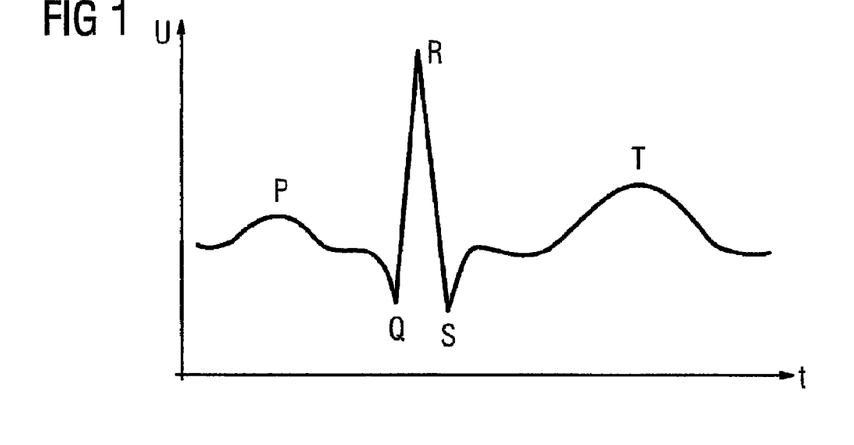
FIG. 1 shows by way of example an ideal waveform of an ECG signal over time.

In an advantageous exemplary embodiment the time interval lies e.g. within the rise of the ECG signal between the points designated by "Q" and "R" (see FIG. 1). If more than one ECG channel 1,2 is recorded, the time interval advantageously begins as soon as the start of the rise between "Q" and "R" is detected in one of the channels 1,2, and ends as soon as the end of said rise is detected in the last of the channels 1,2. This means that the time interval has a duration in the order of approx. 12 to 20 milliseconds, max. 50 to 60 milliseconds, before the R-wave. With such a choice of the time interval, the further analysis of ECG signals within the time interval can be effectively accomplished owing to the signal waveform that is particularly distinctive there, e.g. owing to a relatively large amplitude there and a relatively large first derivative of the signal waveform there, as described below.

Figure 3:
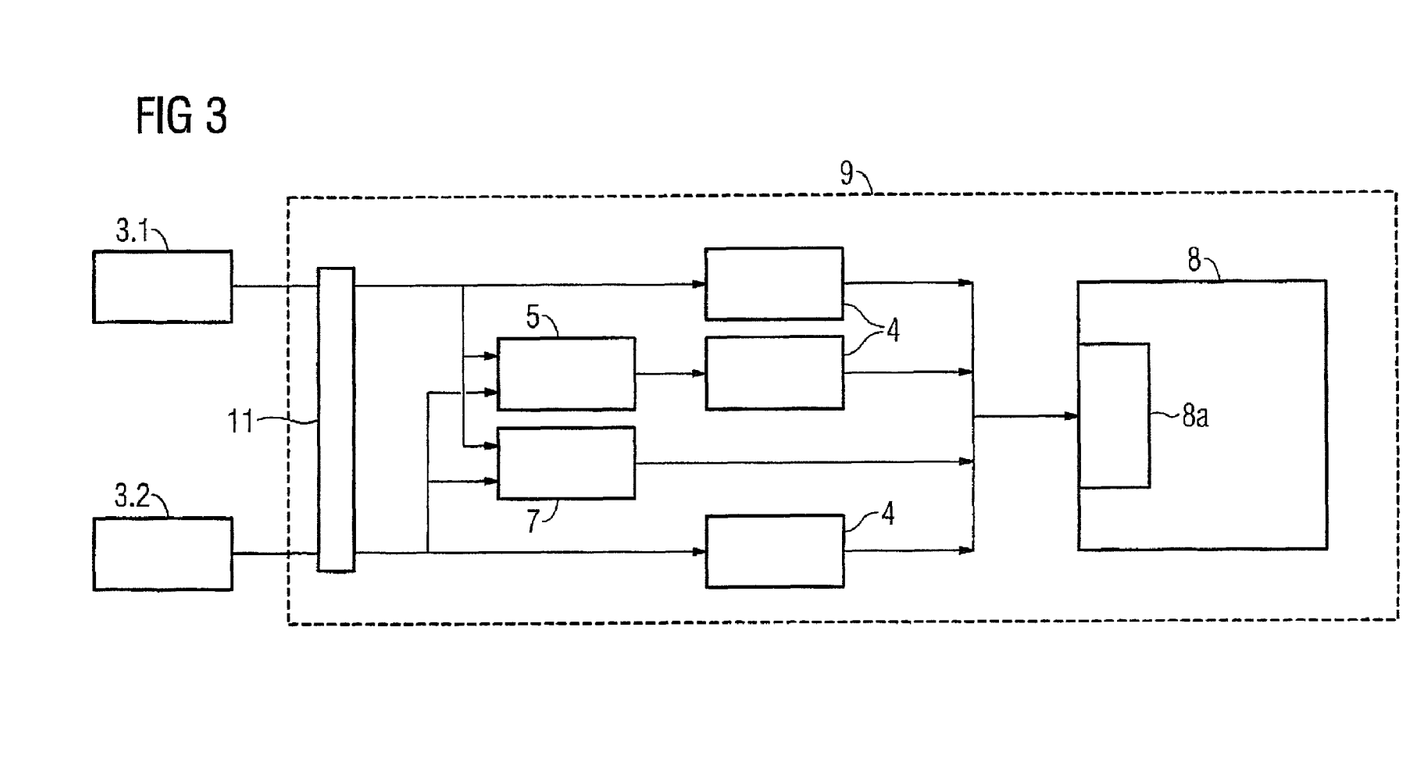

In this case a reference quantity can be determined e.g. as illustrated schematically in FIG. 3. The ECG signals 3.1 and 3.2 acquired from the channels 1 and 2 are supplied to a processing unit 9 which is embodied for the purpose of further processing the ECG signals. Thus, the ECG signal 3.1,3.2 can on the one hand be stored as a possible reference quantity in a memory unit 8a provided it lies in the time interval as it was supplied to the processing unit 9. The reference quantity is therefore simply a signal value over time, i.e. a signal waveform, of a channel of the ECG measuring device. Where appropriate, instead of the entire variation of the ECG signal 3.1,3.2 in the time interval being stored as a reference quantity, only parts of the same will be stored, e.g. individual measurement points in the time profile. Basically, however, maximally comprehensive signal waveforms from the time interval are to be preferred as a more reliable reference quantity to individual measurement points solely on account of the greater volume of data and the averaging over the data that is possible thereby. Furthermore, such an averaging can also be performed over a plurality of recorded signal waveforms of reference ECG signals.

An ECG signal 3.1,3.2 in the processing unit 9 is advantageously supplied to a derivative forming unit 4 which forwards the temporal derivative of the respective ECG signal 3.1,3.2 as a reference quantity to the memory unit 8a. Said temporal derivative can be stored as a reference quantity in addition or alternatively to the storing of the ECG signal 3.1,3.2 itself as a reference quantity. In this case, in addition to a first temporal derivative of the respective ECG signal 3.1,3.2, the derivative forming unit 4 can also calculate a second temporal derivative of the respective ECG signal 3.1, 3.2 and forward it to the memory unit 8a.

If two channels 1 and 2 are used for signal acquisition, these can each be considered separately and/or further reference quantities can be determined from the ECG signals 3.1 and 3.2 which lie within the time interval. In the latter case the ECG signals 3.1 and 3.2 can be supplied, for example, to a magnitude determining unit 5 which computes the common magnitude (Mag) of the two ECG signals 3.1 and 3.2. This is accomplished for example by forming the root, the sum of the squared values of the ECG signals 3.1 and 3.2 (S1 and S2): $Mag = \sqrt{S1^2 + S2^2}$. This can happen particularly simply if the individual ECG signals 3.1,3.2 in the time interval of individual channels 1,2 are advantageously written as components of a vector V=(S1, S2), or, in the case of precisely two channels 1,2, as a complex number Z, where Re{Z}=S1 and Im{Z}=S2. Complex-value vectors are, of course, also possible. The above-described common magnitude can therefore also be designated as the absolute value of the vector V or of the complex number Z. In this case, too, it is possible that not the entire variation of the ECG signal 3.1,3.2 in the time interval will be stored as a reference quantity in the memory unit 8a for the purpose of calculating the common magnitude, but possibly only parts of the same, e.g. individual measurement points in the time profile. If more than two channels 1,2 are measured, e.g. three or more, the common magnitude can be formed analogously by forming the root, the sum of the squared values of the e.g. three or more ECG signals (S1, S2, S3, . . . ) of each measured channel:

$$Mag = \sqrt{(S1^2 + S2^2 + S3^2 + ...)}.$$

Suitable for consideration as a common magnitude are values which record the individual values of the ECG signals used for their calculation as equivalent and therefore express the information of the ECG signals in a common value. As a result of the consideration of a common magnitude, variations, e.g. in an individual measured channel or a small number of measured channels, can advantageously be compensated in a subsequently described comparison of comparative values of measured ECG signals 3.1,3.2 with the reference values. Such an identification of an R-wave, taking into account at least two ECG channels, is therefore particularly robust.

A common magnitude of two or more ECG signals 3.1,3.2 of two or more channels 1,2 of an ECG measuring device 10 of this kind determined by the magnitude determining unit 5 is likewise transmitted to the memory unit 8a for storing as a reference quantity. Alternatively or in addition, the calculated common magnitude can also be supplied initially to a derivative forming unit 4 which passes on the temporal derivative of the common magnitude to the memory unit 8a for storing as a reference value. In this case, too, in addition to a first temporal derivative, a second temporal derivative of the calculated common magnitude can also be determined by the derivative forming unit 4 and forwarded to the memory unit 8a.

An advantage of using the respective first and, where applicable, second temporal derivatives of the described values is that these are not subjected to any offset variations.

A further reference quantity that is advantageously to be determined in addition, when two ECG signals 3.1,3.2 of two channels 1,2 are used, is the determination of a so-called reference angle (RHO_ref) by means of an angle determining unit 7 between the values of the ECG signals (S1 and S2) at the time of the occurrence of the already identified R-wave in the following way:

$$RHO\_ref = \arctan\left(\frac{S1(t = Rwave)}{S2(t = Rwave)}\right).$$

A reference angle determined in this way thus provides information about a phase lag existing between the two channels 1 and 2 due to the respective contacting of the channels with the patient. If, as already suggested above, the individual ECG signals 3.1,3.2 are combined in a vector V or a complex number Z, the phase lag can be illustrated as angle information in the ECG signals represented as trajectories. The phase lag between two channels during an ECG measurement remains constant (within the framework of physiological variations). Thus, an angle RHO determined between measured ECG signals 3.1,3.2 of the channels 1,2 after determination of the reference angle may also not deviate significantly from the reference angle RHO_ref when an R-wave is present, if a variation in the phases of the channels does not occur due to external influences, such as e.g. respiratory movements. Angle information of said kind can thus be advantageously used for further validation of an R-wave detected in the ECG signal measured after the determination of the reference values.

To sum up, therefore, the following were proposed as examples of possible reference quantities determined from the reference ECG signals: the signal values of the reference ECG signals in the time interval or in parts of the same, the first and, where applicable, second temporal derivative of the signal values, a common magnitude in the time interval or in parts of the same, the first and, where applicable, second temporal derivative of the common magnitude and/or a determined reference angle RHO_ref at the time of the occurrence of an R-wave in the reference ECG signal.

In a further step (203c), a comparison rule is generated from the stored reference quantities. This happens in a computing unit 8 which has access to the reference quantities stored in the memory unit 8a and to which subsequently measured ECG signals can be routed, possibly in processed form. As its result the comparison rule indicates how subsequently measured ECG signals in which an R-wave is to be identified must correlate with the reference quantities if an R-wave is present.

For example, the comparison rule thus includes a determination of a deviation of the reference quantity from a corresponding value of a measured ECG signal as its result. This can happen e.g. such that the reference quantities are processed in such a way that e.g. the sum is determined via the error squares of values of the measured ECG signal corresponding to the reference quantities compared to the reference quantities. The error sum of squares is determined e.g. by way of the following formula:

$$SumQ(\tau) = \alpha_S \cdot \sum_{t=0}^{\Delta t} (|X(\tau - \Delta t + t) - LX(t)|)^2,$$

where LX(t) is the reference quantity, X(t) the measured corresponding comparative value, $\Delta t$ the time interval and $\alpha_s$ a normalization factor which ensures that SumQ($\tau$) is equal to zero if X(t) is identical to the previously determined reference quantity LX($\tau$). In this case an advantageous choice of the normalization factor is the reciprocal sum of the squared reference quantity values over the time interval. This value can also be described as the "energy" of the reference quantity in the time interval.

Figures 4, 4A:
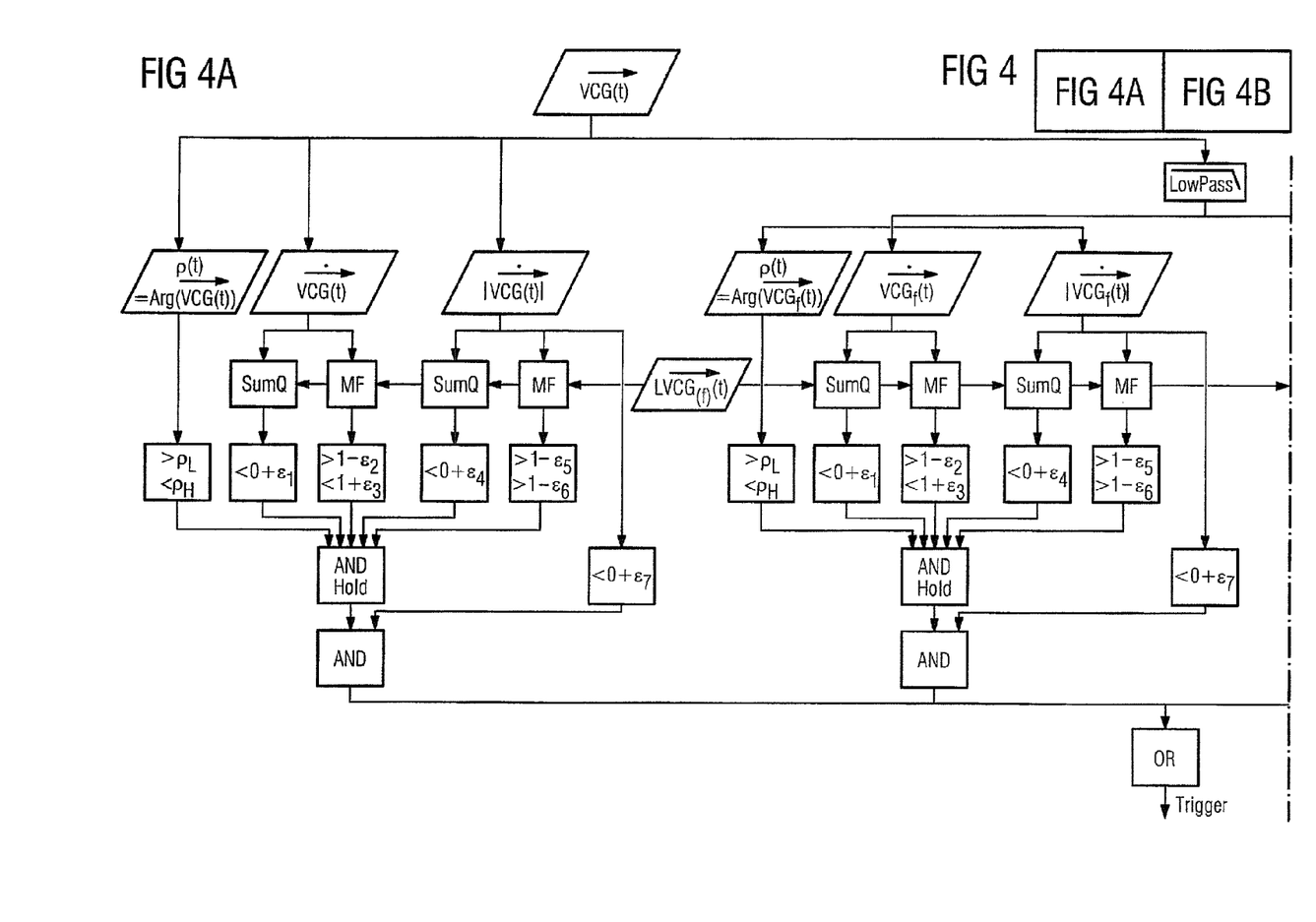
FIG. 4 is a schematic flow diagram of a method according to the invention with a particularly advantageous selection and combination of reference quantities and comparison rules.
Figure 4B:
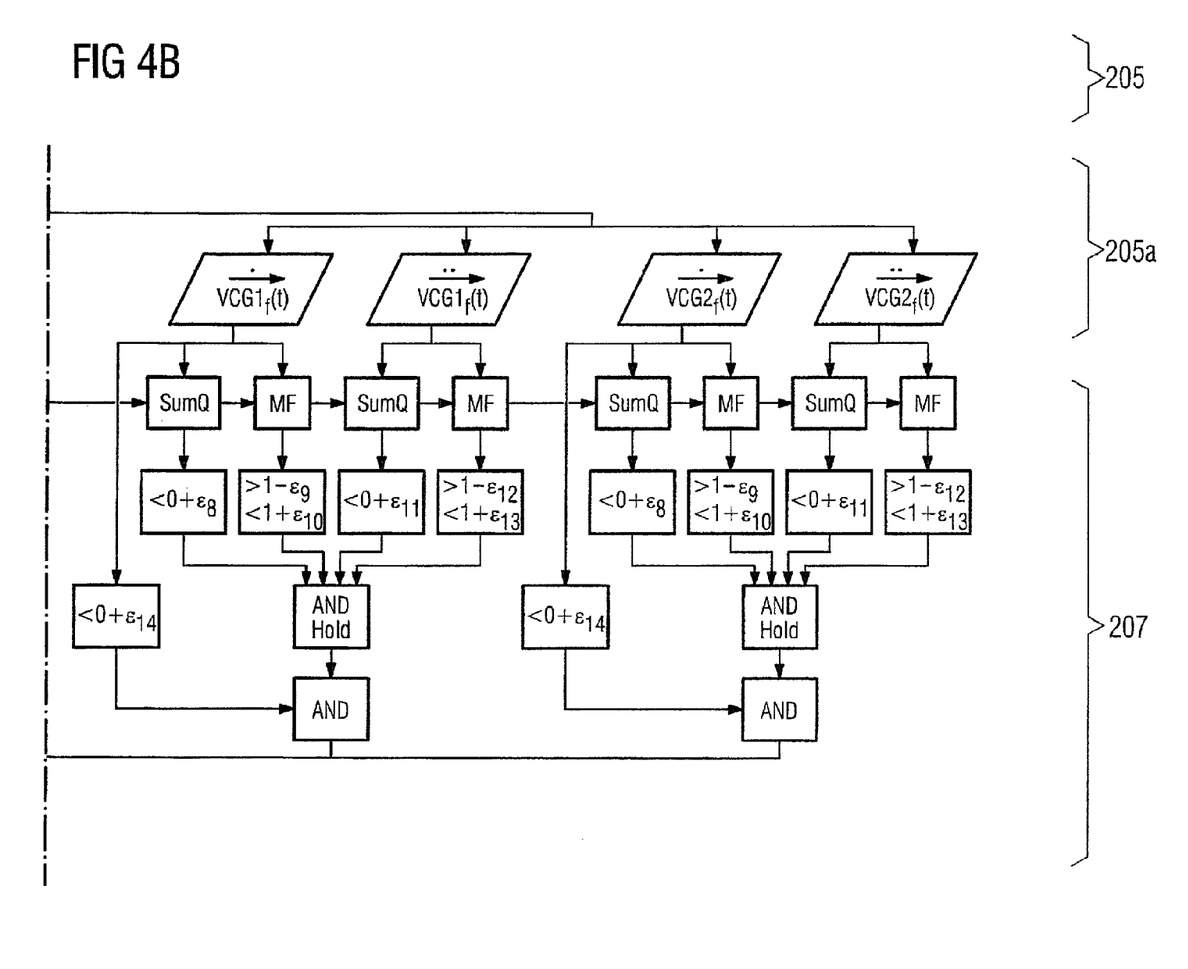

Thus, a positive result of said comparison criterion is a value equal to zero (ideal value) or, as the case may be, a value that deviates from zero at the maximum by a predefinable small threshold value $\epsilon_1, \epsilon_4, \epsilon_8, \epsilon_{11}$ (see also FIG. 4).

A different type of error calculation, such as e.g. the determination of the simple error, for the purpose of determining the deviation is also conceivable, depending on the desired precision. The respective advantages and disadvantages of different error calculations are known.

Alternatively or in addition, the comparison rule can include the use of an optimum filter and output of a similarity value as result. An optimum filter (also called "matched filter", MF) determines the similarity of a curve, in this case e.g. of the waveform of the subsequently measured ECG signal or of a value of the ECG signal corresponding to a reference quantity in the time interval as a comparative value, with a predefined curve, in this case a reference quantity, e.g. the profile of the, e.g. first, temporal derivative of the common magnitude of the reference ECG signals. Mathematically, this advantageously happens through forming of the correlation of reference quantity and corresponding value, e.g. advantageously according to the following formula:

$$MF(\tau) = \alpha \cdot \sum_{i=0}^{\Delta t} X(\tau - \Delta t + t) \cdot LX^*(t),$$

where $LX(t)$ is the reference quantity, $X(t)$ the measured corresponding comparative value, which are in each case represented as a complex-value variable, $\Delta t$ the time interval and $\alpha$ a normalization factor which ensures that $MF(\tau)$ is equal to one if $X(t)$ is identical to the previously determined reference quantity $LX(\tau)$. As is usual with complex numbers, the "*" means that the conjugate-complex variable is used. An advantageous choice of the normalization factor is once again the reciprocal sum of the squared reference quantity values over the time interval. This value can also be described as the "energy" of the reference quantity in the time interval.

A positive result of said comparison criterion is therefore a comparative value equal to one (ideal value) or a value which deviates from one at the maximum by a predefinable small threshold value $\epsilon_2, \epsilon_5, \epsilon_9, \epsilon_{12}$ downward or $\epsilon_3, \epsilon_6, \epsilon_{10}, \epsilon_{13}$ upward. In this case the upper and lower threshold $\epsilon_2, \epsilon_5, \epsilon_9, \epsilon_{12}$ and $\epsilon_3, \epsilon_6, \epsilon_{10}, \epsilon_{13}$, respectively, can, of course, also be chosen as the same size each time (see also FIG. 4).

If, in addition, a reference angle RHO_ref was also determined as a reference quantity, a maximum deviation of an angle RHO determined in the same way in the measured ECG signal can be specified as a further comparison rule. For example, the angle RHO is to lie in a cone around RHO_ref which deviates in each direction at a maximum by an angle range of approx. 65° to 70°.

A measurement of a reference ECG signal and the steps up to the generation of the comparison rule (201, 203a,b,c) are advantageously performed each time after the ECG measuring device 10 is attached to the patient before the measurements that are planned with the magnetic resonance scanner 100 and that require triggering are performed. In particular after the ECG measuring device 10 has been attached to the patient positioned on an examination table of the magnetic resonance scanner, a measurement of a reference ECG signal is performed repeatedly until a displacement of the examination table into the magnet of the magnetic resonance scanner is started. In this way particularly up-to-date reference quantities can be determined after the contacting of the ECG measuring device 10 with the patient has been stabilized as far as possible and no interfering influences of the magnetic field of the magnetic resonance scanner on the ECG measuring device 10 are yet present.

Storing a plurality of reference quantities and using same for generating the comparison rule increases the flexibility and stability of the method. However, it can also suffice to evaluate only one reference quantity, e.g. the temporal derivative, in particular the first temporal derivative, of the signal values or of the common magnitude.

If the reference quantities are known and the comparison rule(s) has(have) been specified, the actual ECG measurement which is to be used for triggering further measurements or examinations, e.g. by means of the magnetic resonance scanner, is started (step 205). From the ECG signals measured in the process, comparative values corresponding to the reference quantities are determined analogously to the approach described with reference to FIG. 3 for determining the reference quantities (step 205a).

Specifically, therefore, the following are determined alternatively or in each case constantly from the measured ECG signals for comparison with the corresponding reference quantities: the signal values of the measured ECG signals, the first and, where applicable, second temporal derivative of the signal values, a common magnitude of the measured ECG signals, the first and, where applicable, second temporal derivative of the common magnitude and/or an angle RHO in the measured ECG signal determined analogously to the reference angle RHO_ref.

These comparative values (signal values and/or first temporal derivative and/or second temporal derivative of the signal values and/or common magnitude and/or first temporal derivative and/or second temporal derivative of the common magnitude and/or angle RHO) are compared with the reference values on the basis of at least one of the above-described comparison rules (step 207).

To sum up, the following variables and reference quantities are proposed for the comparison rules for the purpose of determining a respective deviation:
- the ECG signal values 3.1,3.2 of the measured ECG signals from the corresponding reference quantity and/or
- the first temporal derivative(s) of the measured ECG signal values 3.1,3.2 from the corresponding reference quantity and/or
- the second temporal derivative(s) of the measured ECG signal values 3.1,3.2 from the corresponding reference quantity and/or
- the common magnitude of the measured ECG signal values 3.1,3.2 from the corresponding reference quantity and/or
- the first temporal derivative of the common magnitude of the measured ECG signal values 3.1,3.2 from the corresponding reference quantity and/or
- the second temporal derivative of the common magnitude of the measured ECG signal values 3.1,3.2 from the corresponding reference quantity and/or
- the phase lag of the ECG signals of two channels 1,2 in the form of the determined angle RHO from the reference angle RHO_ref.

In order to determine the deviations of the said variables and reference quantities, in particular for the said ECG signal values 3.1,3.2, the common magnitude and their respective derivatives, the following comparison criteria are proposed in each case:
- error determination, in particular via the error sum of squares as described above and/or
- matched filter, in particular as described above.

Advantageously, both the error determination, in particular via the error sum of squares, and a matched filter are used. In particular when a plurality of channels 1,2 are used for measuring the ECG signal, the sole use of matched filters, for example, is not to be recommended since a result of the matched filter can lie close to the optimum value one even when only one channel yields a result close to the optimum value, although the other channel or channels does or do not.

Also advantageously, reference ECG signals and ECG signals measured before the determination of the reference quantities and before the determination of the comparative values (cf. FIG. 3) are supplied to a smoothing filter 11, a low-pass filter for example, which clears the ECG signals e.g. of sources of radio-frequency interference. With "smoothed" reference values and comparative values obtained in this way, the above-described steps 203c, 207 and 209 can be performed analogously, in particular in addition.

As a condition for the output of a trigger signal, both the results of the above-described comparison with the unsmoothed values and the results of said "smoothed" comparison must be positive ("and" function; "AND") or the results of the two comparisons can be used with an "or" function ("OR") as a condition for the output of a trigger signal.

Through the use of such a smoothing filter 11 the duration of the method is in fact lengthened overall. If necessary, the disadvantage of this longer duration, which lies in the order of approx. 2 to 3 milliseconds, must be weighed against the advantage of interference-free signals for the evaluation.

As already described above, one reference quantity and its comparison with the corresponding comparative value of a measured ECG signal can already be sufficient for the method. However, the reliability of detection of an R-wave is increased with the number of reference quantities checked in the comparison.

Thus, in order to achieve a particularly reliable identification of an R-wave in the measured ECG signals, all the results of the comparison rule must be positive. At least one positive result can, however, also be chosen as sufficient if, for reasons possibly given, the demands in terms of the precision of the identification of the R-wave do not have to satisfy more exacting requirements.

If this is the case and therefore the result or results of the comparison rule is or are positive, in a last step 209 a trigger signal is output which is supplied to the magnetic resonance scanner and there triggers a measurement, e.g. a recording of an image of an organ.

In a particularly advantageous exemplary embodiment, a trigger signal is output in step 209 only if in addition, after confirmation of a sufficient number of positive results of the already described criteria, the first temporal derivative of the common magnitude, or at least of one measured ECG signal value, deviates from zero at the maximum only by a small, predefinable threshold value. With an extreme condition of this kind, the existence of an extreme value in the measured signal waveform, individually or combined across the channels, is identified. Thus, the time of the presence of an R-wave can be determined particularly precisely, since there such an extreme value, a maximum, is present and so the trigger signal can be output particularly precisely.

Similarly advantageously, in the case described in the last paragraph also, a trigger signal is emitted only if a predefinable maximum duration between a confirmation of a sufficient number of positive results on the one hand and the determination of an extreme value in the measured signal waveform on the other hand, is not exceeded. A maximum duration of said kind is advantageously less than or equal to the already described time interval, particularly advantageously in the order of approx. 15 milliseconds.

FIG. 4 is a schematic flow diagram showing an exemplary embodiment of a method according to the invention with an exemplary selection and combination of reference quantities and comparison rules.

In this case ECG signals can be measured as a vector cardiogram (VCG(t)) as described in step 205. As described in step 205a, the comparative values corresponding to the previously determined reference quantities ($LVCG_{(f)}(t)$) can also be determined. In this case, in a branch of the flow diagram shown on the left, the angle ($\rho(t)$), the temporal derivative of the signal ($\overline{\dot{VCG}(t)}$) and the temporal derivative of the common magnitude ($\overline{|\dot{VCG}(t)|}$) can be determined from the measured ECG signals. In a branch of the flow diagram shown on the right, the ECG signal VCG(t) can first be smoothed, in this case by means of a low-pass filter. Then it is possible on the one side (branch to left after low-pass filter) also to determine the just cited variables as comparative values ($\rho(t)$, $\overline{\dot{VCG}_f(t)}$ and $\overline{|\dot{VCG}_f(t)|}$) from the smoothed ECG signal $VCG_f(t)$. The index "f" stands here for "filtered" ("smoothed").

For the comparative values $\overline{\dot{VCG}(t)}$, $\overline{\dot{VCG}_f(t)}$, $\overline{|\dot{VCG}(t)|}$ and $\overline{|\dot{VCG}_f(t)|}$ determined in each case it is possible again in each case using the comparison criteria "error sum of squares" (SumQ) and a matched filter (MF) to carry out a comparison, and using the determined angle $\rho(t)$ to carry out a simple threshold value comparison, in this case with an upper and a lower threshold $\rho_H$ and $\rho_L$, with the aid of the reference quantities $LVCG_{(f)}(t)$ (in this case the index "f" is placed in parentheses, since smoothing was performed, or not, according to the associated comparative values in each case), as described above with reference to step 207.

Furthermore, following the smoothing on the other side (branch to right after low-pass filter) the first temporal derivative of an ECG signal of a first channel $\overline{\dot{VCG}_{1f}(t)}$, the second temporal derivative of the ECG signal of the first channel $\overline{\ddot{VCG}_{1f}(t)}$ and the first and second derivative of an ECG signal of a second channel $\overline{\ddot{VCG}_{2f}(t)}$ $\overline{\ddot{VCG}_{2f}(t)}$ can be determined. Here, once again, a comparison can be performed with the aid of the corresponding reference quantities $LVCG_{(f)}(t)$, as described above with reference to step 207, for the determined comparative values $\overline{\dot{VCG}_{1f}(t)}$, $\overline{\ddot{VCG}_{1f}(t)}$, $\overline{\dot{VCG}_{2f}(t)}$ and $\overline{\ddot{VCG}_{2f}(t)}$ using the comparison criteria "error sum of squares" (SumQ) and a matched filter (MF). This branch demonstrates an advantageous detection of R-waves on the basis of ECG signals of individual channels in each case. This is advantageous in particular in cases in which in one channel or a small number of the channels of the ECG measuring device an ECG signal measured during the desired detection of R-waves does not correspond to the R-wave learned by means of the reference values, though in the other channels it does. This can occur e.g. if during the measurement a patient is required alternately to breathe deeply and hold his/her breath, as a result of which the position of his/her heart can change. In such a case detecting the R-wave via the above-described comparison criteria that operate with comparative values and reference quantities which in each case process the ECG signals of a plurality of channels in a common value, is no longer reliably possible. By checking the ECG signals of the individual channels also, advantageously in addition to the checking of the said common values, a particularly reliable detection of R-waves can be ensured. The additional checking of the second derivative in addition to the first derivative of the ECG signals of individual channels in a performed comparison in turn increases the volume of data and consequently the reliability of the identification of R-waves.

If the result is positive in each branch of the flow diagram for each of the above-described comparisons ("AND Hold"), it is furthermore possible to consider in each branch, as likewise already described above, the first temporal derivative of the common magnitude for the smoothed and unsmoothed values or, as the case may be, the first temporal derivative of the ECG signals of the first and second channel. If in one of the branches ("OR") the condition that said respective first temporal derivative of the common magnitude or, as the case may be, of the ECG signals of the first and second channel deviates from zero only by a small predefinable threshold value $\epsilon_7$ or $\epsilon_{14}$ ("<0+$\epsilon_7$" or "<0+$\epsilon_{14}$") continues to be fulfilled ("AND"), a trigger signal is output.

Owing to the broad selection of the comparison criteria, such an approach of selecting and combining reference quantities and comparative values affords a particularly good validation of the entire method for identifying an R-wave.

The invention claimed is:

1. A method for identifying a R-wave in an ECG signal for triggering a further measurement or examination, comprising:
    measuring a reference ECG signal by an ECG measuring device;
    identifying the R-wave in the reference ECG signal;
    determining a reference quantity from the reference ECG signal, wherein the reference ECG signal is in a time interval that starts before the R-wave and lasts up to an occurrence of the R-wave;
    generating a comparison rule based on the reference quantity;
    measuring the ECG signal in which the R-wave is to be identified;
    comparing the measured ECG signal with the reference quantity based on the comparison rule; and
    outputting a trigger signal based on a positive result of the comparison,
    wherein the comparison rule determines a deviation of the reference quantity from the measured ECG signal,
    wherein the deviation is determined via a determination of an error, and
    wherein the determination of the error is an error sum of squares.

2. The method as claimed in claim 1,
    wherein the ECG measuring device comprises one channel,
    wherein the reference quantity is a signal value of the one channel of the ECG measuring device at a time in the time interval, or
    wherein the reference quantity is a first or a second temporal derivative of the signal value.

3. The method as claimed in claim 1, wherein the trigger signal is output if the deviation is below a predefined threshold value.

4. The method as claimed in claim 1, wherein the reference quantity is determined in a variation over the entire time interval.

5. The method as claimed in claim 1, wherein the comparison rule uses a matched filter and outputs a similarity value.

6. The method as claimed in claim 5, wherein the trigger signal is output if a result of the matched filter deviates from an ideal value of the similarity value of the matched filter by a predefined value.

7. The method as claimed in claim 1,
    wherein the ECG measuring device comprises two channels,
    wherein the reference quantity is a signal value from signal values of the two channels of the ECG measuring device at a time in the time interval, or
    wherein the reference quantity is a first or a second temporal derivative of the signal values.

8. The method as claimed in claim 7, wherein the reference quantity is a common magnitude of the signal values of the two channels.

9. The method as claimed in claim 7, wherein the reference quantity is a reference angle determined from the signal values of the two channels.

10. The method as claimed in claim 9, wherein the trigger signal is output if the measured ECG signal deviates from the reference angle by a predefined angle range.

11. The method as claimed in claim 7,
    wherein the signal values of the two channels or the first or the second temporal derivative of the signal values are represented as complex values,
    wherein real parts of the complex values are the signal values or the first or the second temporal derivative of a first channel,
    wherein imaginary parts of the complex values are the signal values or the first or the second temporal derivative of a second channel.

12. The method as claimed in claim 1, wherein the ECG measuring device comprises a plurality of channels and signal values of the plurality of channels are represented as a vector.

13. The method as claimed in claim 1, wherein a plurality of reference quantities are compared with corresponding measured ECG signals based on the comparison rule.

14. The method as claimed in claim 13, wherein the trigger signal is output if all results of the comparison are positive.

15. The method as claimed in claim 1, wherein a smoothing filter is applied to the reference ECG signal prior to the determination of the reference quantity and is applied to the measured ECG signal prior to the comparison.

16. The method as claimed in claim 1, wherein the trigger signal is output if an extreme condition is fulfilled within a predefined maximum duration in the measured ECG signal after the positive result has been obtained.

17. An ECG measuring device, comprising:
    a processing unit that:
        identifies a R-wave in a reference ECG signal measured by the ECG measuring device,
        determines a reference quantity from the reference ECG signal, wherein the reference ECG signal is in a time interval that starts before the R-wave and lasts up to an occurrence of the R-wave,
        generates a comparison rule based on the reference quantity,
        compares a measured ECG signal in which the R-wave is to be identified with the reference quantity based on the comparison rule, and
        outputs a trigger signal based on a positive result of the comparison,
    wherein the comparison rule determines a deviation of the reference quantity from the measured ECG signal, wherein the deviation is determined via a determination of an error, and wherein the determination of the error is an error sum of squares.

18. The ECG measuring device as claimed in claim 17, wherein the processing unit comprises a smoothing filter.

19. A magnetic resonance scanner, comprising:
an ECG measuring device comprising:
a processing unit that:
identifies a R-wave in a reference ECG signal measured by the ECG measuring device,
determines a reference quantity from the reference ECG signal, wherein the reference ECG signal is in a time interval that starts before the R-wave and lasts up to an occurrence of the R-wave,
generates a comparison rule based on the reference quantity,
compares a measured ECG signal in which the R-wave is to be identified with the reference quantity based on the comparison rule, and
outputs a trigger signal based on a positive result of the comparison to trigger a measurement by the magnetic resonance scanner, wherein the comparison rule determines a deviation of the reference quantity from the measured ECG signal, wherein the deviation is determined via a determination of an error, and wherein the determination of the error is an error sum of squares.

* * * * *